(12) United States Patent
Maxson

(10) Patent No.: US 9,700,327 B2
(45) Date of Patent: Jul. 11, 2017

(54) APPARATUS AND METHOD FOR REPAIRING BONE DEFECTS

(71) Applicant: Biomet Sports Medicine, LLC, Warsaw, IN (US)

(72) Inventor: William Maxson, Fort Wayne, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 13 days.

(21) Appl. No.: 15/016,670

(22) Filed: Feb. 5, 2016

(65) Prior Publication Data

US 2016/0151077 A1    Jun. 2, 2016

Related U.S. Application Data

(62) Division of application No. 13/757,077, filed on Feb. 1, 2013, now Pat. No. 9,289,222.

(51) Int. Cl.
| | |
|---|---|
| *A61B 17/00* | (2006.01) |
| *A61B 17/16* | (2006.01) |
| *A61B 17/17* | (2006.01) |
| *A61F 2/38* | (2006.01) |

(52) U.S. Cl.
CPC ...... *A61B 17/1675* (2013.01); *A61B 17/1697* (2013.01); *A61B 17/1764* (2013.01); *A61B 2017/1602* (2013.01); *A61F 2/3877* (2013.01)

(58) Field of Classification Search
None
See application file for complete search history.

(56) References Cited

U.S. PATENT DOCUMENTS

| 5,312,411 A | 5/1994 | Steele et al. |
| 5,324,295 A | 6/1994 | Shapiro |
| 5,417,695 A | 5/1995 | Axelson, Jr. |

(Continued)

FOREIGN PATENT DOCUMENTS

| DE | 19501550 A1 | 7/1996 |
| WO | WO-2008098061 A2 | 8/2008 |
| WO | WO-2014120999 A1 | 8/2014 |

OTHER PUBLICATIONS

"U.S. Appl. No. 13/757,077, Final Office Action mailed Aug. 4, 2015", 8 pgs.

(Continued)

*Primary Examiner* — Sameh Boles
(74) *Attorney, Agent, or Firm* — Schwegman Lundberg & Woessner, P.A.

(57) ABSTRACT

A system can include a sizing and drill guide having a body with a bone engaging side, an opposite side and first and second guide holes. The bone engaging side can include a profile for positioning in the trochlear groove and the guide holes can include axes that can be orientated at an acute angle. Retaining members can be positioned in bores formed in the body and can fix the guide to the femur. A cutting device can be guided by the guide holes and can include a bone engaging end having a body and first and second cutting portions. The first cutting portion can have a smaller diameter than the second cutting portion and can be axially spaced apart therefrom so as to form a stepped pocket in the femur. The body can include an outer diameter sized to be complimentary to an inner diameter of the guide holes.

13 Claims, 10 Drawing Sheets

(56) References Cited

U.S. PATENT DOCUMENTS

| | | | |
|---|---|---|---|
| 5,716,360 | A | 2/1998 | Baldwin et al. |
| 6,277,121 | B1 | 8/2001 | Burkinshaw et al. |
| 7,695,477 | B2 | 4/2010 | Creger et al. |
| 2002/0183760 | A1 | 12/2002 | Mcgovern et al. |
| 2010/0036383 | A1 | 2/2010 | Major et al. |
| 2010/0191245 | A1 | 7/2010 | Ek et al. |
| 2010/0222782 | A1 | 9/2010 | Collazo et al. |
| 2011/0009964 | A1 | 1/2011 | Schwartz et al. |
| 2012/0209278 | A1* | 8/2012 | Ries .................. A61F 2/3877 606/96 |
| 2012/0259335 | A1 | 10/2012 | Scifert et al. |
| 2014/0222002 | A1 | 8/2014 | Maxson |

OTHER PUBLICATIONS

"U.S. Appl. No. 13/757,077, Non Final Office Action mailed Feb. 2, 2015", 11 pgs.

"U.S. Appl. No. 13/757,077, Notice of Allowance mailed Nov. 12, 2015", 5 pgs.

"U.S. Appl. No. 13/757,077, filed Jun. 2, 2015 to Non Final Office Action mailed Feb. 2, 2015", 19 pgs.

"U.S. Appl. No. 13/757,077, filed Oct. 5, 2015 to Final Office Action mailed Aug. 4, 2015", 12 pgs.

"U.S. Appl. No. 13/757,077, Response filed Dec. 9, 2014 to Restriction Requirement mailed Oct. 9, 2014", 15 pgs.

"U.S. Appl. No. 13/757,077, Restriction Requirement mailed Oct. 9, 2014", 8 pgs.

"European Application Serial No. 14705258.3, Communication pursuant to Rules 161(1) and 162 EPC mailed Sep. 18, 2015", 2 pgs.

"International Application Serial No. PCT/US2014/014001, International Preliminary Report on Patentability mailed Aug. 13, 2015", 10 pgs.

"International Application Serial No. PCT/US2014/014001, International Search Report Apr. 1, 2014", 5 pgs.

"International Application Serial No. PCT/US2014/014001, Written Opinion mailed Apr. 1, 2014", 7 pgs.

U.S. Appl. No. 13/757,077, filed Feb. 1, 2013, Apparatus and Method for Repairing Bone Defects.

* cited by examiner

APPARATUS AND METHOD FOR REPAIRING BONE DEFECTS

CLAIM OF PRIORITY

This application is a divisional of U.S. patent application Ser. No. 13/757,077, filed on Feb. 1, 2013, the benefit of priority of which is claimed hereby, and which is incorporated by reference herein in its entirety.

FIELD

The present disclosure relates generally to an apparatus and method for repairing soft tissue and/or bone defects and, more particularly, to an apparatus and method for repairing cartilage and/or bone defects in a knee joint.

BACKGROUND

This section provides background information related to the present disclosure which is not necessarily prior art.

Articular cartilage enables bones to move smoothly relative to one another, as is known in the art. Damage to articular cartilage, such as in a knee joint, can be caused by injury, such as tearing, by excessive wear, or by a lifetime of use. Such damage to the articular cartilage can also cause damage to the underlying bone. The damaged articular cartilage can lead to, in certain circumstances, pain and reduced mobility. Various surgical procedures have been developed to repair damaged articular cartilage, such as microfracture, mosaicplasty or a uni-condyle or partial knee replacement.

While these surgical procedures are effective for their intended purpose, there remains a need for improvement in the relevant art for treating focal defects in articular cartilage in a minimally invasive manner.

SUMMARY

This section provides a general summary of the disclosure, and is not a comprehensive disclosure of its full scope or all of its features.

In one form, a system for use in repairing a soft tissue or bone defect is provided according to the teachings of the present disclosure. The system can include a combined sizing and drill guide, a retaining member and a cutting device. The combined sizing and drill guide can be adapted to be positioned relative to a trochlear groove of a femur. The guide can include a body having a bone engaging side, an opposite side and can define first and second guide holes. The bone engaging side can include a profile adapted to be positioned in the trochlear groove and the first and second guide holes can include respective first and second axes that can be orientated at an acute angle relative to each other. The retaining member can be configured to be positioned in a retaining bore formed in the body, and the retaining members can be adapted to selectively fix the guide to the femur. The cutting device can be configured to be selectively guided by the first and second guide holes. The cutting device can include a bone engaging end having a body, a first cutting portion and a second cutting portion. The first cutting portion can have a smaller diameter than the second cutting portion and can be axially spaced apart therefrom so as to be adapted to form a stepped pocket in the femur. The body can include an outer diameter sized to be complimentary to an inner diameter of the first and second guide holes.

In another form, a method for repairing a soft tissue or bone defect is provided according to the teachings of the present disclosure. The method can include selecting a combined sizing and drill guide having a bone engaging profile sized and shaped to mate with a trochlear groove of a patient. The combined sizing and drill guide can be selected from a plurality of sizing and drill guides having different bone engaging side profiles. The selected guide can be positioned relative to the trochlear groove of the femur. A superior stepped pocket portion can be formed in the femur by guiding a reaming device relative to a superior guide hole in the combined sizing and drill guide, and an inferior stepped pocket portion can be formed in the femur by guiding the reaming device relative to an inferior guide hole of the guide. The superior and inferior stepped pocket portions can form a stepped trochlear groove pocket in the femur. A femoral implant can be positioned in the trochlear groove pocket, where the femoral implant can correspond to the selected combined sizing and drill guide.

In yet another form, a system for use in repairing a soft tissue or bone defect is provided according to the teachings of the present disclosure. The system can include a combined sizing and drill guide, a drill bit, a retaining member and a reaming device. The combined sizing and drill guide can be adapted to be positioned relative to a trochlear groove of a femur. The guide can include a body having a bone engaging side and an opposite side, first and second guide holes extending through the body, and first and second cannulated guide members extending from the opposite side and aligning with the respective first and second guide holes. The bone engaging side can include a profile adapted to be positioned in the trochlear groove and the first and second guide holes and corresponding guide members can include respective first and second axes that are orientated at an acute angle relative to each other. The drill bit can be configured to be guided by the first and second guide holes and corresponding guide members to form first and second bores in the femur. The retaining member can be configured to be positioned in one of the first and second guide holes and corresponding guide members and can be adapted to be positioned in the corresponding bore formed in the femur. The reaming device can include a bone engaging end having a body with a first cutting portion, a second cutting portion and a guide member extending axially from the first cutting portion. The first cutting portion can have a smaller diameter than the second cutting portion and can be axially spaced apart therefrom so as to be adapted to form a stepped pocket in the femur, where the guide member can be adapted to be positioned in the first and second bores.

In still another form, a method for repairing a soft tissue or bone defect is provided according to the teachings of the present disclosure. The method can include selecting a combined sizing and drill guide having a bone engaging profile sized and shaped to mate with a trochlear groove of a patient. The combined sizing and drill guide can be selected from a plurality of sizing and drill guides having different bone engaging side profiles. The selected guide can be positioned relative to the trochlear groove of the femur. A superior guide bore can be formed in the femur by guiding a cutting device relative to a superior guide hole and cannulated guide member of the combined sizing and drill guide, and an inferior guide bore can be formed in the femur by guiding the cutting device relative to an inferior guide hole and cannulated guide member of the guide. The combined sizing and drill guide can be removed from the femur. A superior stepped pocket portion can be formed in the femur by guiding a reaming device relative to and using the superior guide bore, and an inferior stepped pocket portion can be formed in the femur by guiding the reaming device relative to and using the inferior guide bore. The superior and inferior stepped pocket portions can form a stepped trochlear groove pocket in the femur. A selected femoral implant can be positioned in the trochlear groove pocket, where the selected femoral implant can correspond to the selected combined sizing and drill guide.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

Figure 19:
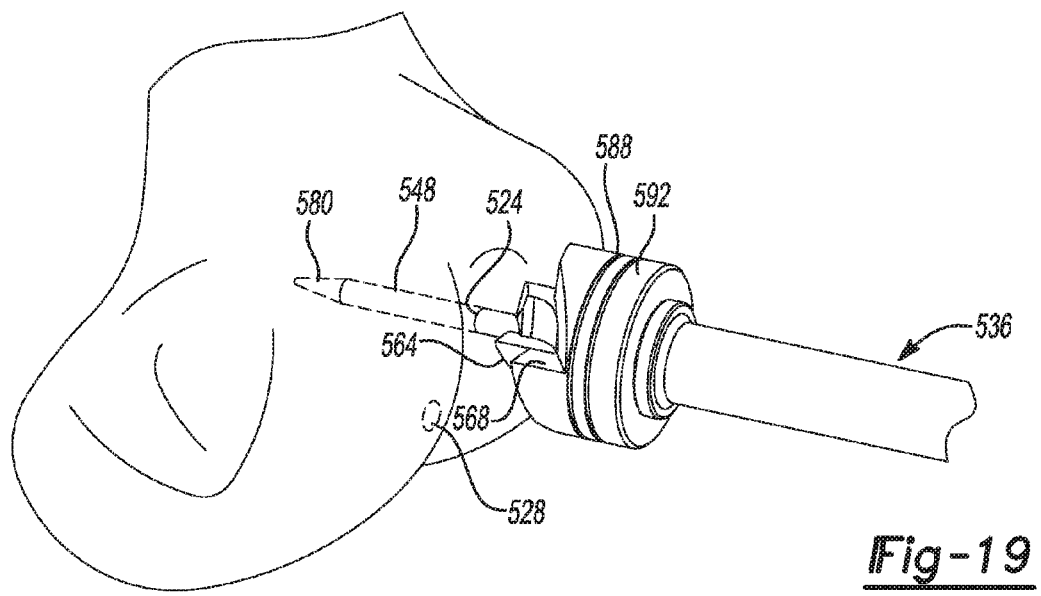
Figure 20:
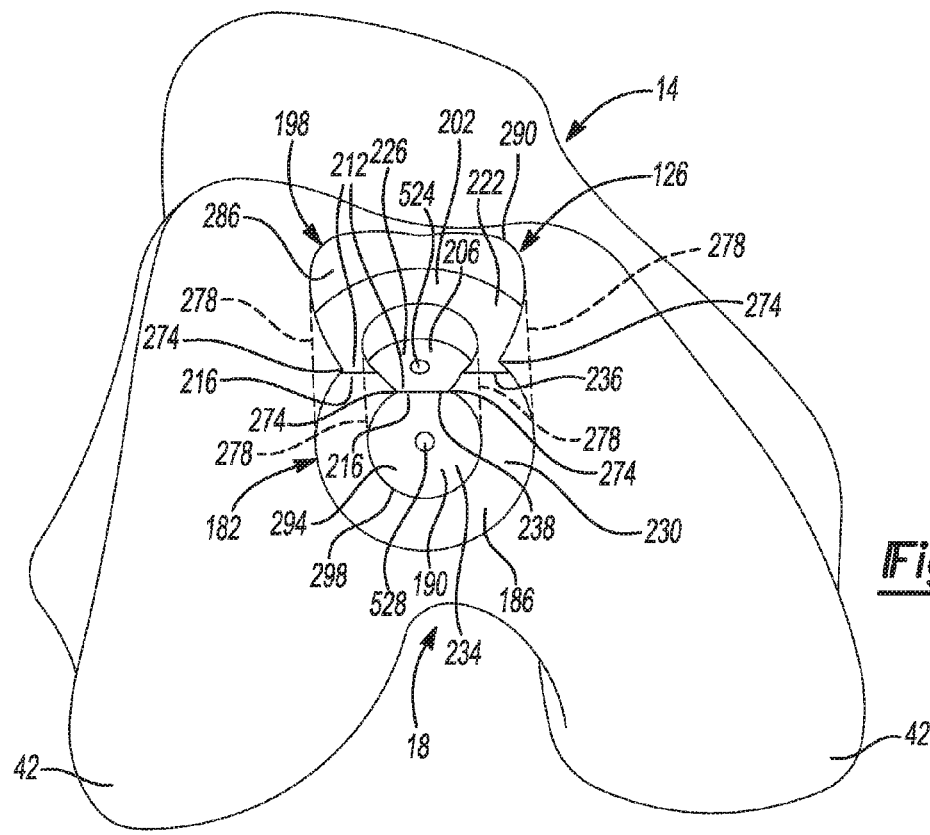

FIG. 19 is a perspective view of the exemplary procedure depicting the drill bit guided by the first bore to form a portion of a pocket in the femur in accordance with the teachings of the present disclosure; and FIG. 20 is a perspective view of the exemplary procedure depicting a pocket formed relative to the trochlear groove defect in the femur in accordance with the teachings of the present disclosure.

DETAILED DESCRIPTION

The following description is merely exemplary in nature and is not intended to limit the present disclosure, its application, or uses. It should be understood that throughout the drawings, corresponding reference numerals indicate like or corresponding parts and features. Although the following description is related generally to methods and systems for repairing a cartilage defect in a femur, it should be appreciated that the methods and systems discussed herein can be applicable to other bones and/or joints of the anatomy.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Turning now to FIGS. 1-20, various methods and systems are disclosed in accordance with the present teachings for repairing a cartilage defect 10 in a femur 14 of a knee joint. As will be discussed in greater detail below, pockets in the femur 14 can be formed using various sizing drill guides for receiving femoral or cartilage resurfacing implants. In accordance with various aspects of the present teachings, the pocket can be formed relative to a defect in the trochlear groove 18 area of the femur 14.

Figure 1:
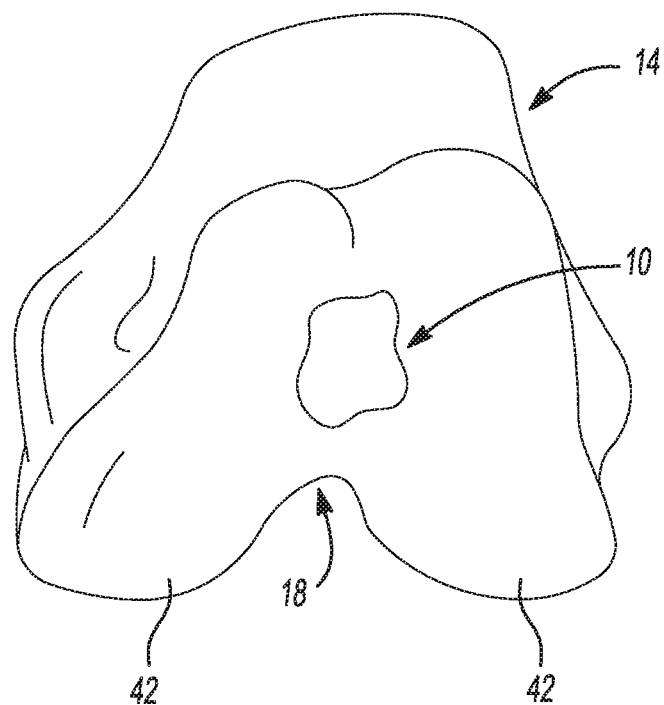
FIG. 1 is a perspective view depicting an exemplary cartilage and/or bone defect in a trochlear groove of a femur in accordance with the teachings of the present disclosure.
Figure 2:
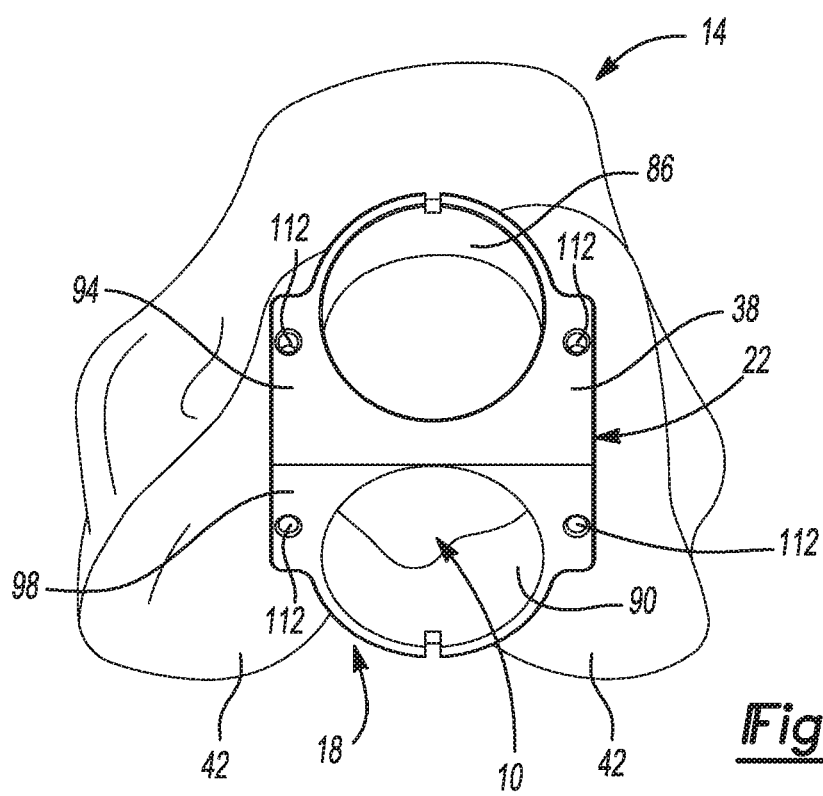
FIG. 2 is a perspective view depicting an exemplary surgical procedure including positioning an exemplary sizing drill guide relative to the trochlear groove and defect in accordance with the teachings of the present disclosure.

With particular reference to FIGS. 1 and 2, the femur 14 is shown having an exemplary defect 10 in the trochlear groove 18. It should be appreciated that the size and location of defect 10 can vary from the size and position shown in FIG. 1. As can be seen in FIG. 2, a sizing drill guide 22 can be positioned relative to the defect 10 and trochlear groove 18. As will be discussed in greater detail below, sizing drill guide 22 can be used to determine an appropriate size and location for a femoral implant 28 (e.g., FIGS. 6A-6C).

Figure 3:
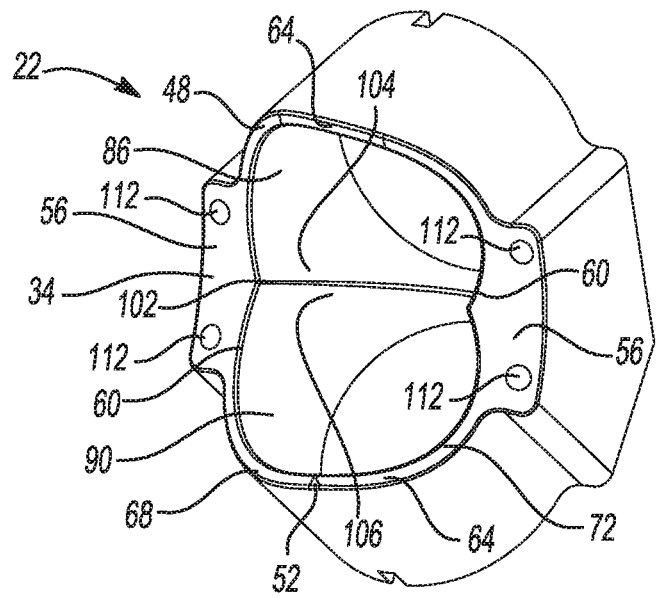
FIG. 3 is a rear perspective view of the sizing drill guide of FIG. 2 in accordance with the teachings of the present disclosure.
Figure 4:
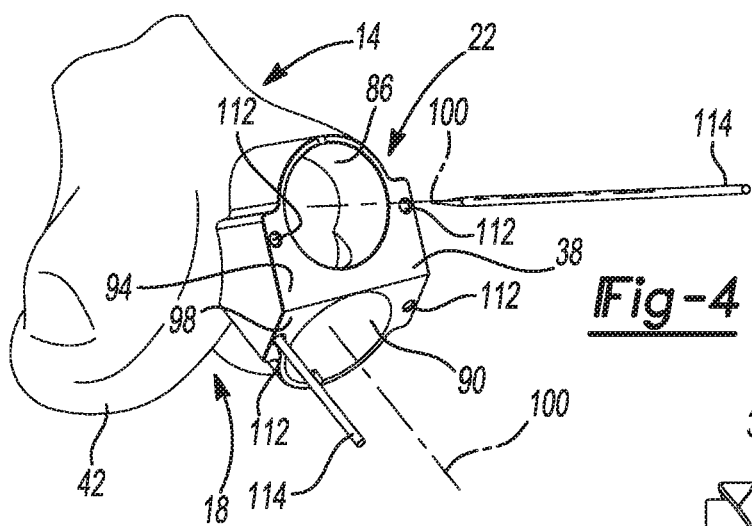
FIG. 4 is a perspective view of the exemplary procedure depicting positioning guide pins relative to the sizing drill guide and the femur in accordance with the teachings of the present disclosure.
Figure 5:
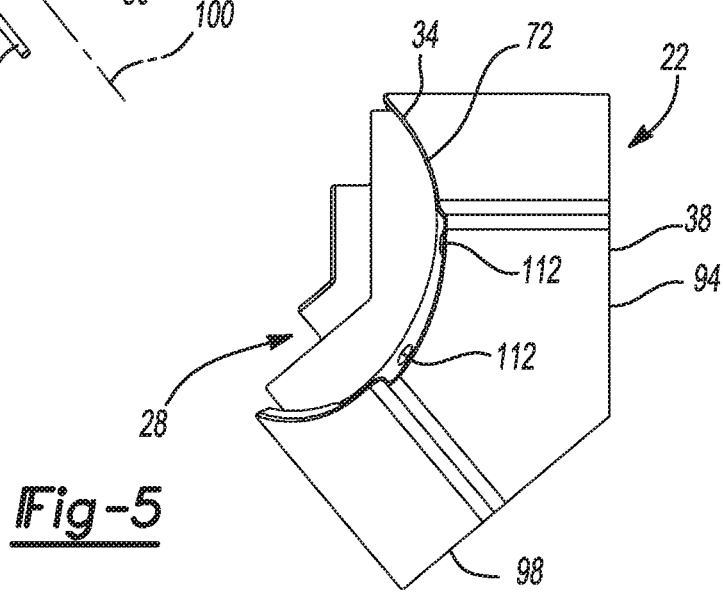
FIG. 5 is a side view depicting an exemplary implant positioned relative to a bone facing side of the sizing drill guide in accordance with the teachings of the present disclosure.

With additional reference to FIGS. 2-5, sizing drill guide 22 can include a first or bone engaging side or surface 34 and an opposite second side 38. The bone engaging surface 34 can include an arcuate shape to match a contour of the trochlear groove 18 and the adjacent condyles 42. The arcuate shape can be arcuate in both the anterior-posterior plane and the medial-lateral plane. In one exemplary aspect, the arcuate shape can be concave in the anterior-posterior plane and convex in the medial-lateral plane. The bone engaging side 34 can include an upper or superior end 48, an opposite lower or inferior end 52 and opposed lateral sides 56. In the exemplary configuration shown in FIG. 3, the bone engaging side 34 can include an arcuate shape or profile 60 in the superior-inferior direction and an arcuate shape or profile 64 in a medial-lateral direction forming an outer perimeter 68 of bone engaging side 34 relative to the superior and inferior ends 48, 52. In one exemplary aspect, the bone engaging side 34 can include an overall profile 72 that is complimentary or a negative of an articular surface 78 of the femoral implant 28, as generally shown in FIG. 5 with reference to FIG. 6C.

Figure 14:
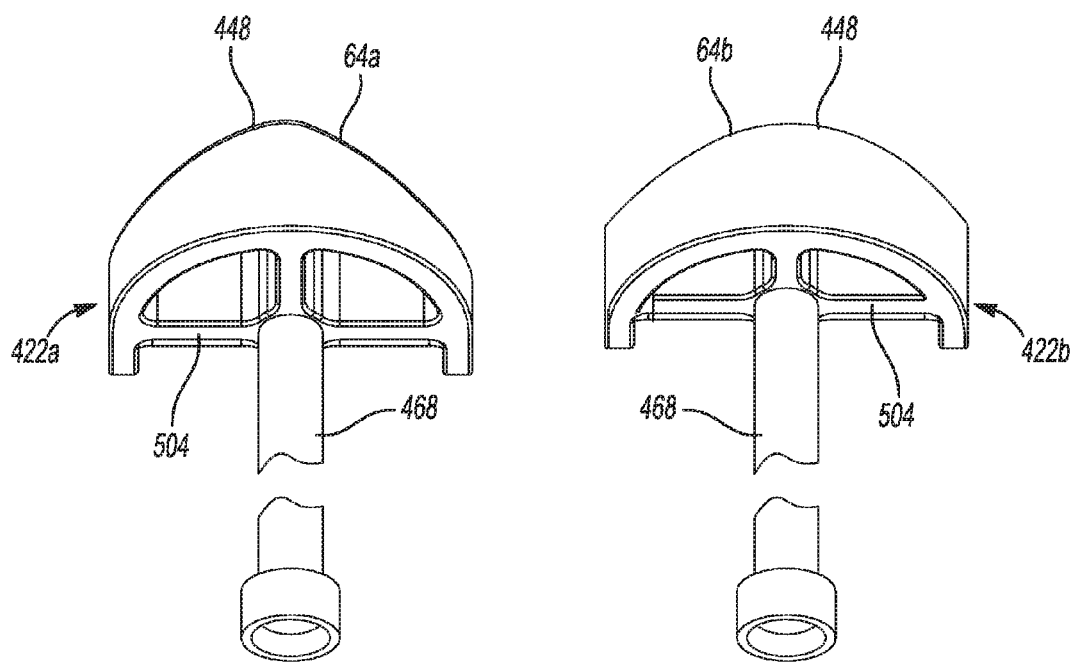
FIG. 14 is a perspective view depicting two different exemplary sizing drill guides in accordance with the teachings of the present disclosure.
Figure 15:
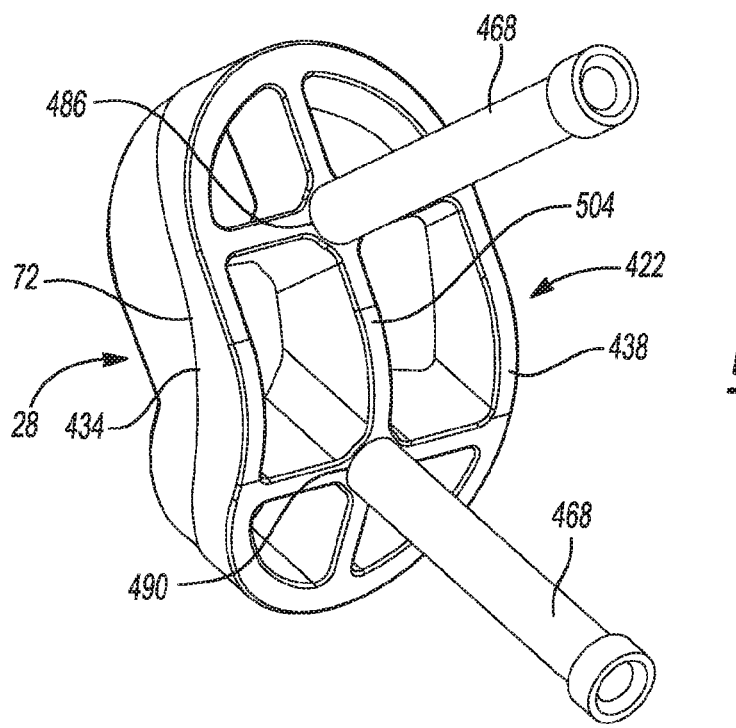
FIG. 15 is a perspective view depicting the exemplary implant of FIGS. 5-6C positioned relative to a bone facing side of the sizing drill guide of FIG. 12 in accordance with the teachings of the present disclosure.

In one exemplary aspect, sizing drill guide 22 can be provided in a set having a variety of different sizes that correspond to a variety of correspondingly sized femoral implants so as to best match the size of the patient's cartilage defect and the anatomical configuration of the patient's trochlear groove. For example, sizing drill guide 22 can be provided in various different sized footprints having varying lengths and/or widths, as well as various different shaped profiles 64 for each such varying footprint size of guide 22. One example of such a varying profile or arcuate shape 64 is shown in FIG. 15 with reference to a sizing drill guide 422. As can be seen in FIG. 14, sizing drill guide 422A includes a first profile or arcuate shape 64A having a smaller radius of curvature for a smaller knee and sizing drill guide 422B has a second profile or arcuate shape 64B having a larger radius of curvature for a larger knee while each of guides 422A, 422B can include the same overall footprint or perimeter size.

According to various aspects of the present teachings, the various different sizes and profiles of sizing drill guide 22 can be based on data generated from scans of various non-patient human knees. In one exemplary aspect, approximately 1500 scans of such knees can be used to generate the data for sizing drill guides 22. In this aspect, the sizing drill guide 22 can be provided in two distinct footprint sizes with eight unique profiles 64 of bone engaging side 34 for each size that substantially replicate the anatomic trochlear groove for both the left and right knees. The femoral implant 28 can be provided in each of the various sizes and profiles discussed above such that the articular surface 78 can closely mimic the natural anatomy of the patient's knee without having to measure any portion of the patient's knee.

The sizing drill guide 22 can include an upper or superior cylindrical guide hole 86 and a lower or inferior cylindrical guide hole 90, each sized and shaped to receive a reamer for forming an implant receiving pocket in the distal end of femur 14, as will be discussed below. The second side 38 of sizing drill guide 22 can include an upper or superior surface 94 surrounding or substantially surrounding superior guide hole 86 and an inferior surface 98 surrounding or substantially surrounding guide hole 90. In the exemplary configuration illustrated, the surfaces 94, 98 can be planar surfaces configured to receive or engage a stop collar, as will also be discussed below. The superior and inferior guide holes 86, 90 can be positioned at an acute angle relative to each other as shown for example in FIGS. 4 and 5. Similarly, the surrounding surfaces 94, 98 can be angled relative to each other and perpendicular or substantially perpendicular to an axis 100 (FIG. 4) of the respective guide holes 86, 90. The axes 100 can be angled at an acute angle relative to each other.

In accordance with various aspects of the present teachings, the guide holes 86, 90 can be spaced apart from each other on the second side 38 while overlapping on the bone engaging side 34, as shown for example in FIGS. 3 and 4. In one exemplary aspect, the guide holes 86, 90 can overlap at an interior point 102 such that each of the guide holes 86, 90 can be truncated. In particular, an inferior portion 104 of superior guide hole 86 can be truncated and a superior portion 106 of inferior guide hole 90 can be truncated, as shown in FIG. 3. In other words, each of the guide holes 86, 90 can be truncated by each other on the bone engaging side 34. As will be discussed in greater detail below, such a truncated configuration of guide holes 86, 90 can form an overlapping or truncated bore pattern in a pocket formed in the femur 14.

A pair of bores 112 can be positioned on opposite lateral sides of each guide hole 86, 90, as shown for example in FIGS. 2-4. Bores 112 can receive guide pins, as will be discussed below in greater detail. In this regard, it should be appreciated that more or less bores 112 can be provided in sizing drill guide 22. For example, one guide bore 112 can be positioned relative to superior guide hole 86, such as in an upper medial side location, and one other guide bore 112 can be positioned relative to inferior guide hole 90, such as in a lower lateral location. Regardless, in the exemplary configuration illustrated with four guide bores 112, it should be appreciated that less than all of the guide bores 112 may be utilized in an associated surgical procedure.

Once an appropriate sizing drill guide 22 has been selected that has a size corresponding to the size of defect 10 or that best matches with the size of the defect 10 and a bone engaging side overall profile 72 that corresponds to the anatomical configuration of the trochlear groove 18, the bone engaging side 34 can be positioned over defect 10 such that the profiles 64 nest in trochlear groove 18, as shown for example in FIGS. 2 and 4. With the sizing drill guide 22 positioned as discussed above, a retaining member or guide pin 114, such as a K-wire with a threaded distal tip, can be inserted into each of the guide bores 112 and into the femur to fix the position of sizing drill guide 22 to the femur 14 about defect 10. As discussed above, one or two guide pins 114 can be positioned in each of the pair of guide bores 112 such that at least one guide pin 114 is positioned relative to each of the superior and inferior guide holes 86, 90.

With the sizing drill guide 22 selected and positioned relative to the trochlear groove 18 and defect 10 as discussed above, the sizing drill guide can now serve as a drill guide to form a pocket for receiving the femoral implant 28 corresponding to the selected guide 22. As will be discussed in greater detail below, a reamer can be guided by guide holes 86, 90 to form portions of a pocket formed to receive femoral implant 28.

Figure 7:
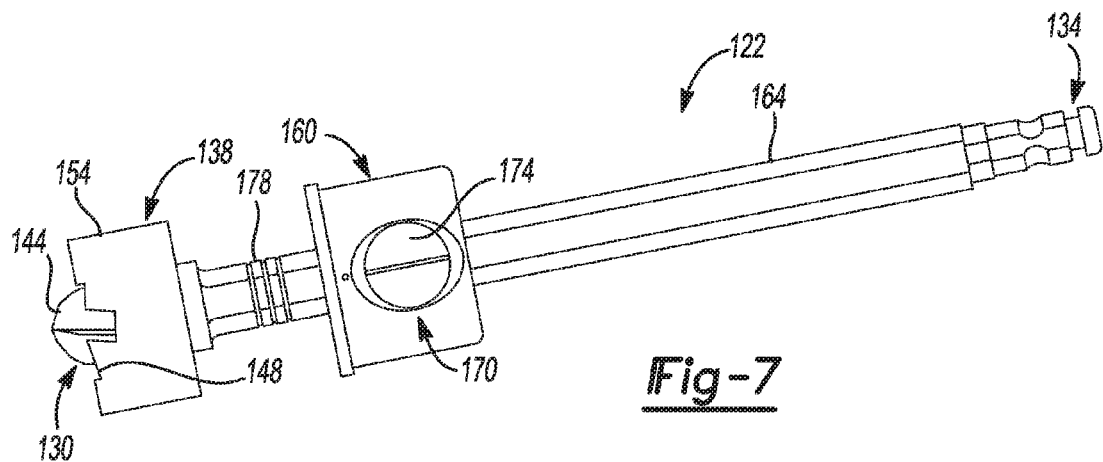
FIG. 7 is a perspective view of an exemplary drill bit or reamer in accordance with the teachings of the present disclosure.
Figure 8:
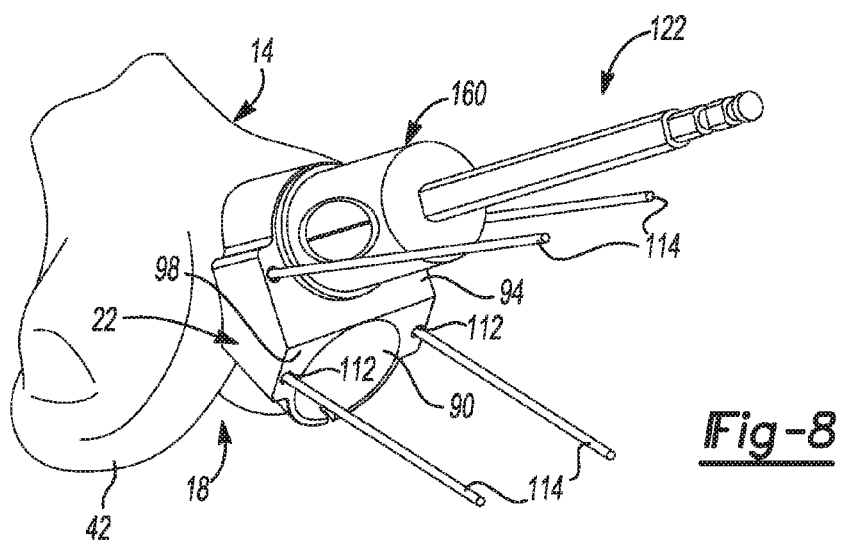
FIG. 8 is a perspective view of the exemplary procedure depicting the drill bit guided by the sizing drill guide to form a portion of a pocket in the femur in accordance with the teachings of the present disclosure.
Figure 9:
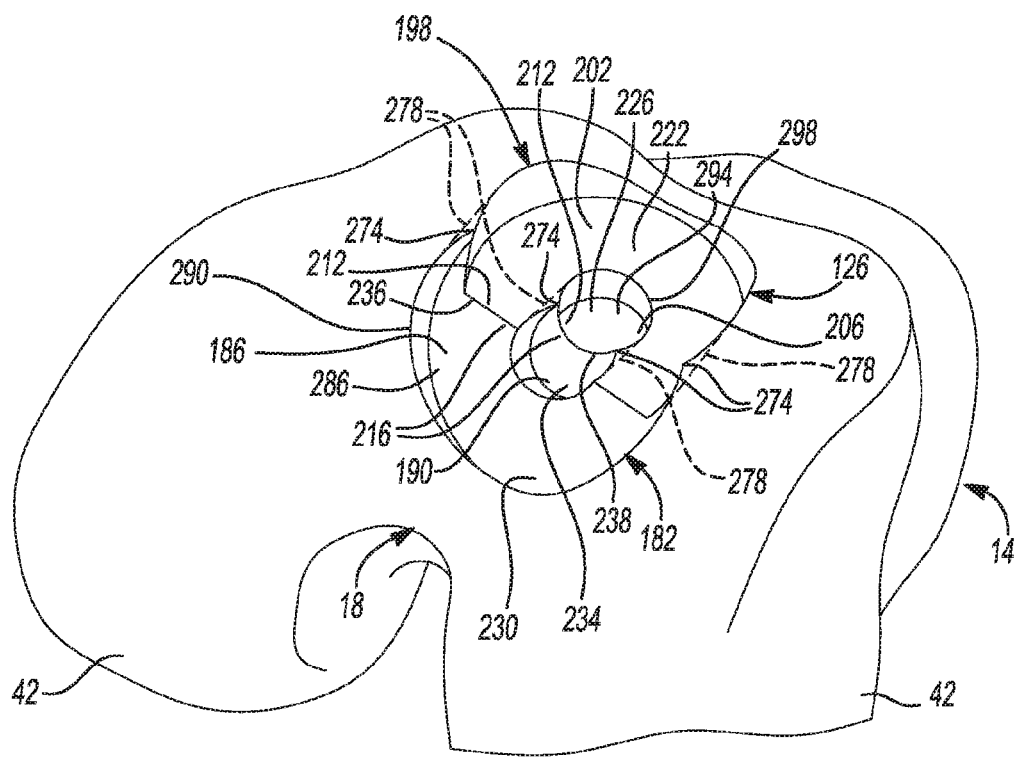
FIG. 9 is a perspective view of the exemplary procedure depicting a pocket formed relative to the trochlear groove defect in the femur using the sizing drill guide and drill bit in accordance with the teachings of the present disclosure.

With additional reference to FIGS. 7-9, a reamer 122 can be guided by guide holes 86, 90 to form portions of the femoral or trochlear pocket 126 (FIG. 9) for receiving femoral implant 28. The reamer 122 can include a first or distal bone engaging end 130 and an opposite second or proximal driving end 134 configured to be coupled to a driver, such as a drill or other rotary driving instrument. The first end 130 can include a cutting, milling or reaming arrangement 138 including a first cutting blade arrangement 144 and a second cutting blade arrangement 148. As can be seen in FIG. 7, the first cutting blade arrangement 144 can be concentric to and of a smaller diameter than the second cutting blade arrangement 148. In addition, in the exemplary configuration illustrated, the first cutting blade arrangement 144 can be axially spaced apart from the second cutting blade arrangement 148 so as to form a stepped pocket configuration in trochlear pocket 126, as will be discussed in greater detail below.

The first end 130 of reamer 122 can also include an outer or perimeter wall 154 complimentary in diameter to an inner diameter of the guide holes 86, 90 and of a sufficient axial length such that the first end 130 can be slidably and rotatably received in and guided by the guide holes 86, 90. The reamer 122 can also include a depth control mechanism, such as a stop collar 160, as also shown in FIG. 7. The stop collar 160 can be selectively axially slidable relative to a shaft 164 of reamer 122 and can include a locking feature 170 configured to set a position of the stop collar 160 along shaft 164 relative to the first end 130. In one exemplary configuration, the locking feature 170 can include a push button 174 configured to provide for adjustment and selective locking of the stop collar 160 axially along shaft 164. The shaft 164 can include indicia, such as annular grooves 178, corresponding to predetermined axial positions for stop collar 160. These positions can correspond to different sizing drill guides 22, and thus to implants 28, such that the implant can be implanted flush or substantially flush with the surrounding articular cartilage of the femur. In one exemplary configuration, the annular grooves 178 can each include a different color that can be coordinated with relevant sizing drill guides 22 for ease of use during a surgical procedure.

In use, reamer 122 can be separately positioned in each of guide holes 86, 90 to form the stepped pocket configuration show in FIG. 9. In one exemplary aspect of the present teachings, the bone engaging end 130 of reamer 122 can be inserted first into the inferior guide hole 90 and advanced relative to sizing drill guide 22 until the prepositioned stop collar engages the inferior surface 98. With reference to FIG. 9, this action can form an inferior pocket portion 182 of the stepped trochlear pocket 126. In particular, the inferior pocket portion 182 of stepped trochlear pocket 126 formed by this action can include an inferior outer bore 186 and an inferior inner bore 190 corresponding to the respective first and second cutting blade arrangements 144, 148. As can be seen in FIG. 9, the inferior inner bore 190 is formed at a greater depth than the inferior outer bore 186 relative to the articular surface of the femur 14 and includes a smaller diameter than inferior outer bore 186.

Upon forming the inferior pocket portion 182, the reamer 122 can be removed from the inferior guide hole 90 and positioned in the superior guide hole 86 while the sizing drill guide 22 remains secured to the femur 14. In a similar manner to the inferior guide hole 90, the bone engaging end 130 of reamer 122 can be advanced relative to guide hole 86 to ream a superior pocket portion 198 of trochlear pocket 126 relative to trochlear groove 18. The superior pocket portion 198 can likewise include a superior outer bore 202 and a superior inner bore 206 axially spaced apart from and smaller than superior outer bore 202, as shown in FIG. 9. The superior bores 202, 206 can be concentric bores having a stepped configuration that forms a shoulder orthogonal to an axis of the bores. Similarly, the inferior bores 186, 190 can be concentric bores having a stepped configuration that forms a shoulder orthogonal to an axis of the bores.

As can be seen in FIG. 9, the trochlear pocket 126 can include portions of the superior pocket portion 198 overlapping with portions of the inferior pocket portion 182. In particular, an inferior portion 212 of the superior outer and inner bores 202, 206 can overlap with a superior portion 216 of the inferior outer and inner bores 186, 190. As can also be seen in FIG. 9, the superior outer and inner bores 202, 206 can form respective parallel planar surfaces 222, 226 that are angled relative to corresponding respective planar parallel surfaces 230, 234 of the inferior outer and inner bores 186, 190. In one exemplary configuration, the angle can be an acute angle. The planar surfaces 222 and 230 can meet forming an edge 236 and the planar surfaces 226, 234 can meet forming an edge 238, as also shown in FIG. 9.

Once the inferior and superior pocket portions 182, 198 have been formed, the reamer 122 can be removed from sizing drill guide 22 and the sizing drill guide 22 can be removed from the femur 14. To remove sizing drill guide 22 from femur 14, the inferior two guide pins 114 can be removed while maintaining the superior two guide pins 114 secured to the femur 14. By maintaining the two superior guide pins 114 connected to the femur 14 in their original position, the sizing drill guide 22 can be removed and, if necessary, repositioned on the femur and trochlear groove in the same original position through use of the superior guide pins 114.

Figure 8A:
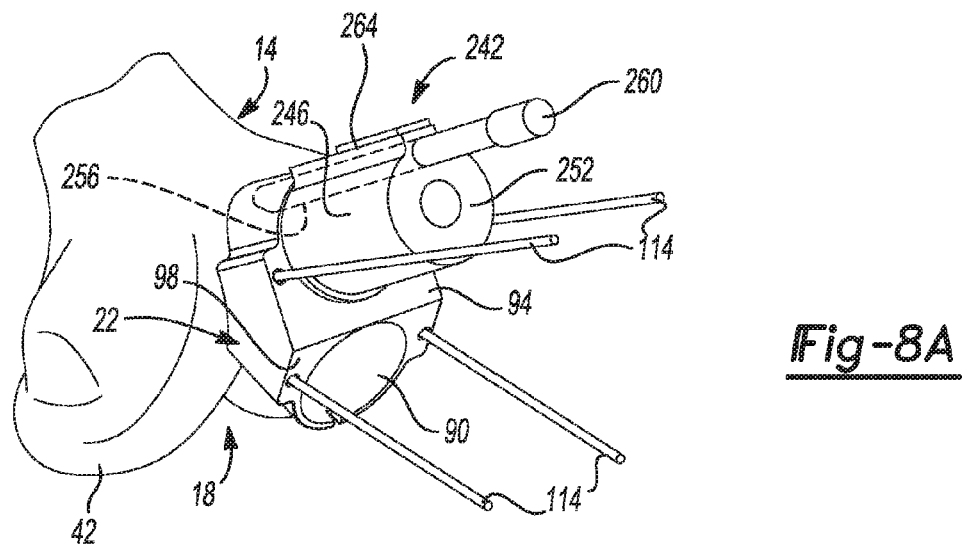
FIG. 8A is a perspective view of the exemplary procedure depicting an exemplary optional depth gauge positioned relative to the sizing drill guide and the defect in the femur in accordance with the teachings of the present disclosure.

With particular reference to FIG. 8A, an option depth gauge 242 can be used in the surgical technique. Optional depth gauge 242 can be used in various instances, such as with a universal reamer not including a stop collar and/or a universal sizing drill guide that may not include a plurality of sizing options. Depth gauge 242 can include a body 246 having an outer dimension greater than an inner diameter of the guide holes 86, 90 such that it can rest on the superior and inferior surfaces 94, 98, as generally shown in FIG. 8A. In one exemplary configuration, body 246 can be in the form of an annular ring or collar 252 with a through bore 256 configured to receive a depth member 260. The depth member 260 can be advanced or retracted relative to body 246 via bore 256 and held in a desired position via a locking arrangement 264.

In operation, depth gauge 242 can be placed on one of the sizing guide surfaces, such as superior guide hole surface 94 shown in FIG. 8A. The depth member 260 can be advanced into guide hole 86 until it engages a portion of the trochlear groove 18. The position of depth member 260 relative to body 246 can be maintained via locking arrangement 264 and can correspond to a depth measurement for reaming the superior pocket portion of trochlear pocket 126 with a reamer after removal of the depth gauge 242 from guide 22.

With reference back to FIG. 9, once the trochlear pocket 126 has been formed as discussed above, corners 274 of the trochlear pocket 126 can be removed to form linear or straight sides 278 (shown in phantom). In particular, the straight sides 278 can be formed on the lateral sides of trochlear pocket 126 and substantially in the areas of overlap between the inferior and superior pocket portions 182, 198.

Once the corners 274 are removed, the trochlear pocket 126 can include an outer pocket 286 with a first outer perimeter 290 corresponding to the outer bores 186, 202 and outer straight sides 278 and an inner pocket 294 with a second outer perimeter 298 corresponding to inner bores 190, 206 and inner straight sides 278.

Figure 6A:
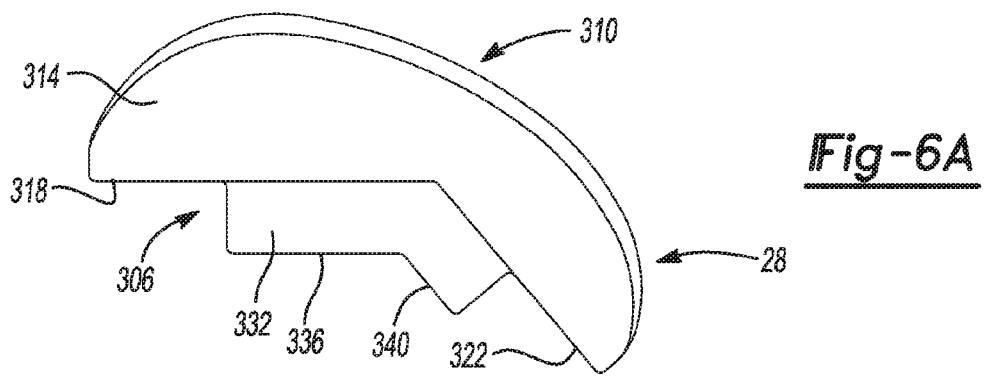
FIG. 6A is a side view of the exemplary implant of FIG. 5 in accordance with the teachings of the present disclosure.
Figure 6B:
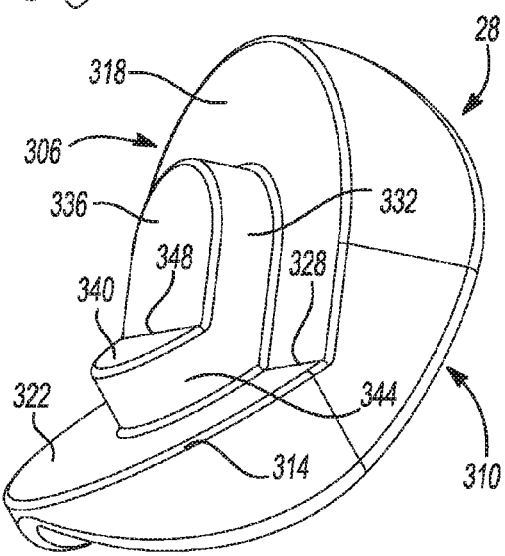
FIG. 6B is a rear perspective view of the implant of FIG. 5 in accordance with the teachings of the present disclosure.
Figure 6C:
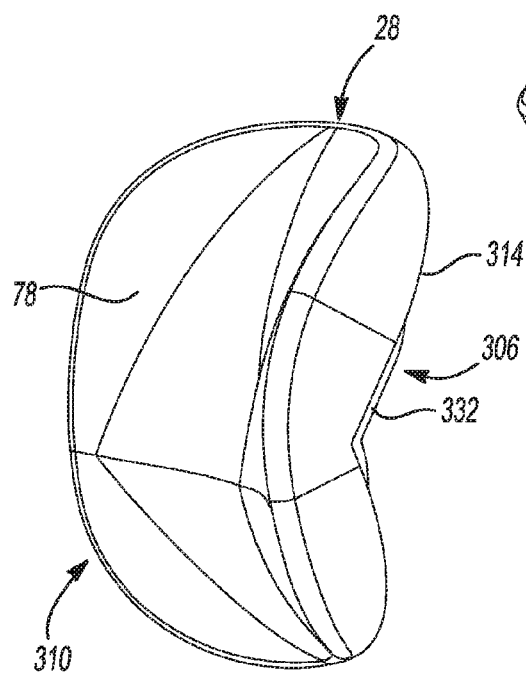
FIG. 6C is a front perspective view of the implant of FIG. 5 in accordance with the teachings of the present disclosure.
Figure 10:
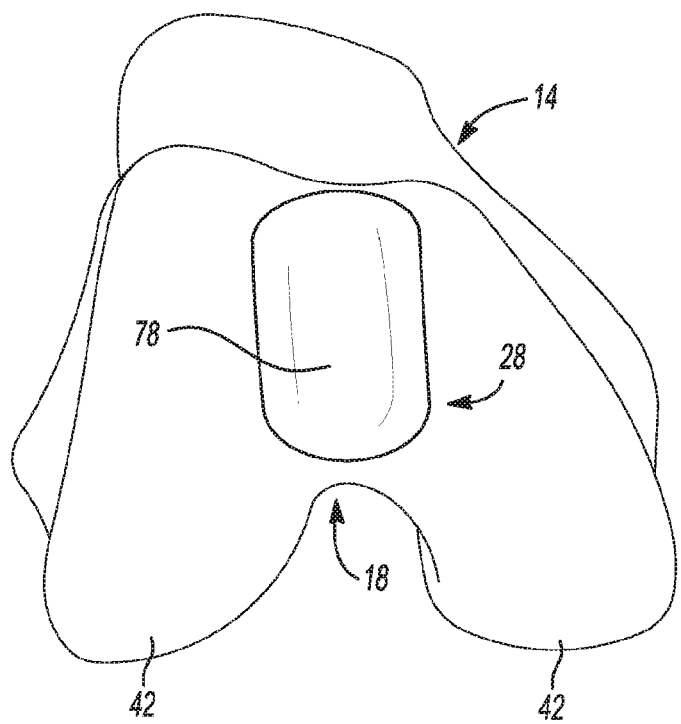
FIG. 10 is a perspective view of the exemplary procedure depicting positioning a femoral implant relative to the pocket in accordance with the teachings of the present disclosure.

Turning now to FIGS. 6A-6C, and with additional reference to FIGS. 9-10, preparation for and implantation of the femoral or trochlear groove implant 28 will now be discussed in greater detail. Femoral implant 28 can include a bone engaging side 306 and an opposite articular surface side 310. The articular surface side 310 can correspond to the bone engaging end 130 of sizing drill guide 22 such that upon implantation, articular surface 78 can be flush with the surrounding articular cartilage of femur 14 and mimic the natural geometry of the patient's trochlear groove area 18.

The bone engaging side 306 can include a first superior surface 318 and a first inferior surface 322 that are sized and shaped to correspond with the planar surfaces 222, 230 of the respective superior and inferior outer bores 202, 186, as shown for example in FIG. 6B. Implant 28 can include an outer perimeter 314 establishing an outer boundary of the surfaces 318, 322 and sized and shaped to match the first outer perimeter 290 of trochlear pocket 126. The surfaces 318, 322 can include planar surfaces and can meet at an edge 328 corresponding to edge 236 of outer pocket 286.

A projection 332 can extend from surfaces 318, 322 and can be sized and shaped to be received in the inner pocket 294. Projection 332 can include a second superior surface 336 and a second inferior surface 340 that can form a second outer perimeter 344 sized and shaped to match the second outer perimeter 298 of inner pocket 294. Similar to the surfaces 318, 322, the surfaces 336, 340 can be planar surfaces angled relative to each other and meeting at an edge 348 corresponding to edge 238 of inner pocket 294.

With continuing reference to FIGS. 6A-6C and 9-10, once the trochlear pocket 126 is formed with the sides 278, a trial corresponding to the selected sizing drill guide can be positioned in the trochlear pocket 126 to check for proper fit. If the trial does not fit flush with the surrounding articular cartilage and/or does not align flush with the planar surfaces 222, 226, 230 and 234, adjustment of the pocket 126 may be required. In this scenario, additional rasping may be required and/or the selected sizing drill guide 22 may be repositioned over the superior guide pins 114 to place guide 22 in the original location used to form guide holes 86, 90. If the selected sizing drill guide 22 is repositioned for additional reaming, the stop collar 160 on reamer 122 may be adjusted to provide for additional depth of pocket 126. Depending on the adjustment that may be required for pocket 126, another sizing drill guide 22 may be positioned over existing guide pins 114 and the procedure discussed above repeated.

Once proper fit of the selected trial is established, the trial can be removed and trochlear pocket 126 can be cleaned and prepared for implantation of implant 28 sized to correspond to the selected sizing drill guide 22. Bone cement can then be applied to the prepared trochlear pocket 126 and/or the bone engaging side 306 of selected implant 28. With the bone cement appropriately applied, the selected implant 28 can be implanted into the prepared trochlear pocket 126 while ensuring that the articular surface 78 is flush with the surrounding native cartilage, as shown for example in FIG. 10. It should be appreciated that implant 28 can alternatively be implanted without bone cement.

In the exemplary configuration illustrated, the bone engaging side 306 of femoral implant 28, once implanted, can align with and engage the geometry of the prepared trochlear pocket 126. For example, the first superior and inferior surfaces 318, 322 of implant 28 can mate with the surfaces 222, 230 of outer bores 202, 186. Similarly, the second superior and inferior surfaces 336, 340 of projection 332 can mate with surfaces 226, 234 of the superior and inferior inner bores 206, 190. The edges 236, 238 of pocket 126 can likewise align with the edges 328, 348 of implant 28.

Figure 11:
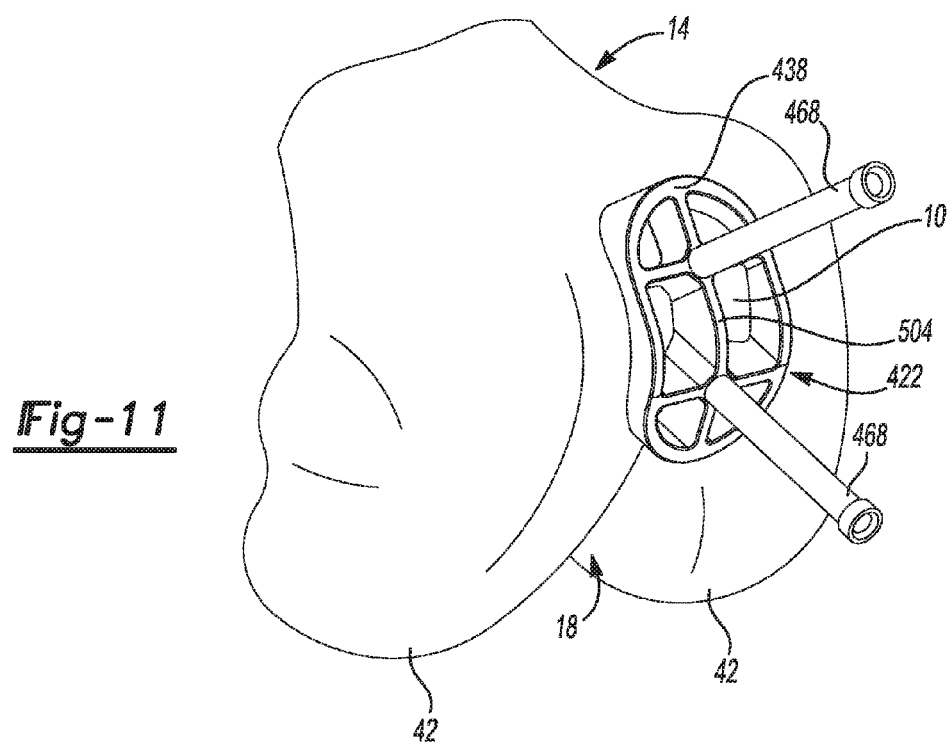
FIG. 11 is a perspective view depicting an exemplary surgical procedure including positioning an exemplary sizing drill guide relative to the trochlear groove and defect in accordance with the teachings of the present disclosure.

Turning now to FIGS. 11-20, another exemplary system and procedure for forming trochlear pocket 126 for receiving a selected implant 28 will now be discussed. As can be seen in FIG. 11, a sizing drill guide 422 can be positioned relative to the defect 10 and trochlear groove 18. Similar to sizing drill guide 22 discussed above, sizing drill guide 422 can be used to determine an appropriate size, profile and location for the femoral implant 28 (e.g., FIGS. 6A-6C).

Figure 12:
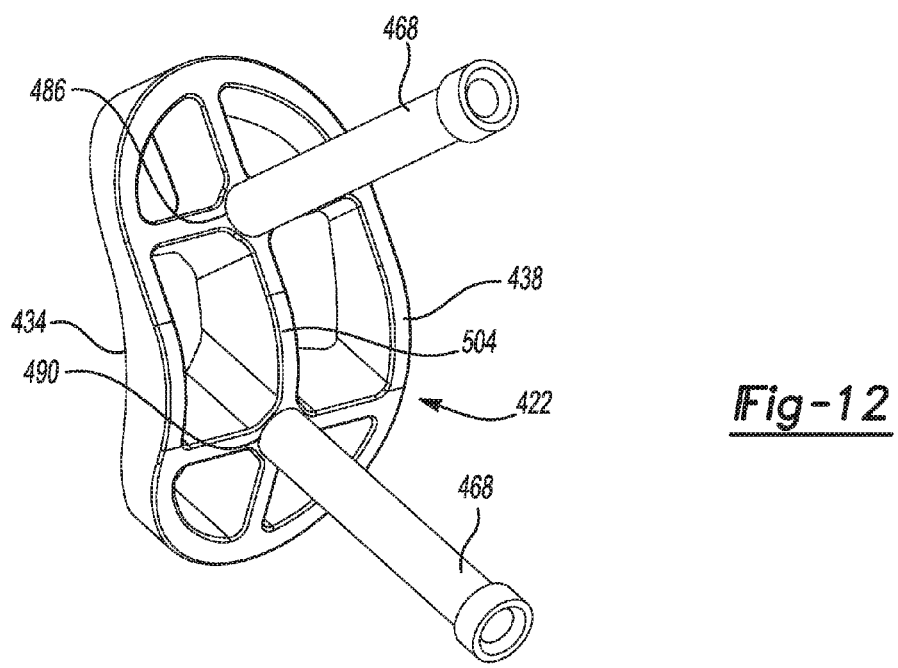
FIG. 12 is a front perspective view of the exemplary sizing drill guide of FIG. 11 in accordance with the teachings of the present disclosure.
Figure 13:
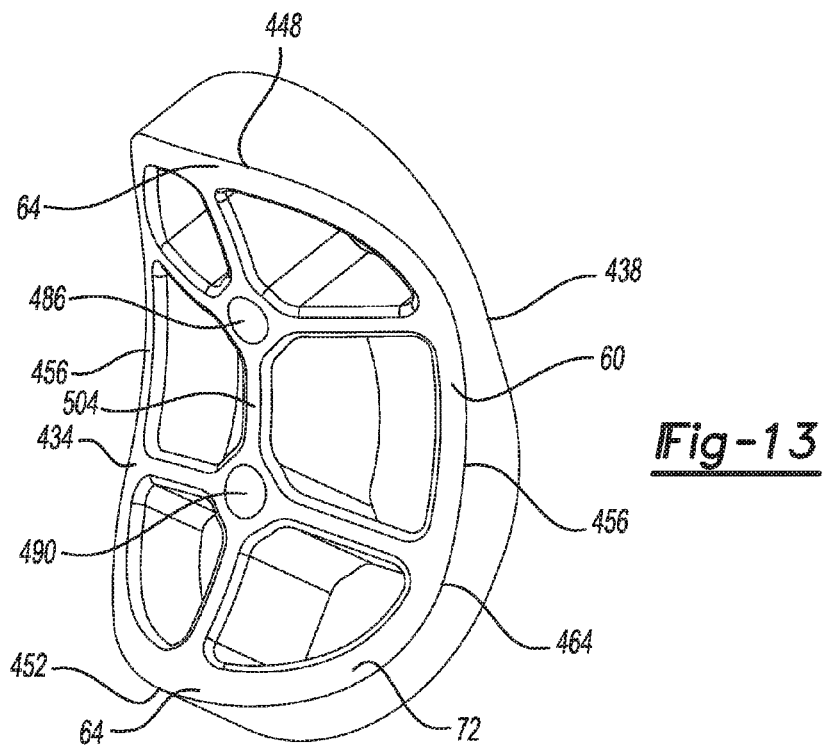
FIG. 13 is a rear perspective view of the sizing drill guide of FIG. 12 in accordance with the teachings of the present disclosure.

With additional reference to FIGS. 12-13, sizing drill guide 422 can include a first or bone engaging side or surface 434 and an opposite second side 438. The bone engaging surface 434 can include an arcuate shape and/or profile to match a contour of the trochlear groove 18 and the adjacent condyles 42. The bone engaging side 434 can include an upper or superior end 448, an opposite lower or inferior end 452 and opposed lateral sides 456. In the exemplary configuration shown in FIG. 13, the bone engaging side 434 can include an arcuate shape or profile 60 in the superior-inferior direction and an arcuate shape or profile 64 in a medial-lateral direction forming an outer perimeter 464 of bone engaging side 434 relative to the superior and inferior ends 448, 452. In one exemplary aspect, the bone engaging side 434 can include an overall profile 72 that is complimentary or a negative of the articular surface 78 of the femoral implant 28, as generally shown in FIG. 15.

In one exemplary aspect, sizing drill guide 422 can be provided in a variety of different sizes similar to sizing drill guide 22. For example, sizing drill guide 422 can be similarly provided in various different sized footprints having varying lengths and/or widths, as well as various different shaped profiles 64 for each such varying footprint size of guide 422. One example of such a varying profile or arcuate shape 64 is shown in FIG. 14 with reference to a sizing drill guide 422A. As can be seen in FIG. 14, sizing drill guide 422A includes a first profile or arcuate shape 64A having a smaller radius of curvature for a smaller knee and sizing drill guide 422B has a second profile or arcuate shape 64B having a larger radius of curvature for a larger knee while each of guides 422A, 422B can include the same overall footprint size. In a similar manner as sizing drill guide 22, the various different sizes and profiles of sizing drill guide 422 can be based on data generated from scans of various human knees.

The sizing drill guide 422 can include an upper or superior guide hole 486 and a lower or inferior guide hole 490 (FIG. 13), each sized and shaped to receive a drill bit, as will be discussed below. A cannulated guide member 468 can extend from each of the guide holes 486, 490. The cannulated guide members 468 can be integrally formed with the sizing drill guide 422 or can be separate components that can be coupled thereto, such as via threading. The cannulated guide members 468 along with the respective guide holes 486, 490 can be orientated at an acute angle relative to each other, similar to sizing drill guide 22.

In the exemplary configuration illustrated, the sizing drill guide 422 can include a webbing or waffle pattern 504 extending between the outer perimeter 464 and the guide holes 486, 490, as generally shown in FIG. 13. Such a pattern 504 can provide structure to the sizing drill guide while also providing for visualization of the defect and/or trochlear groove area 18.

Figure 16:
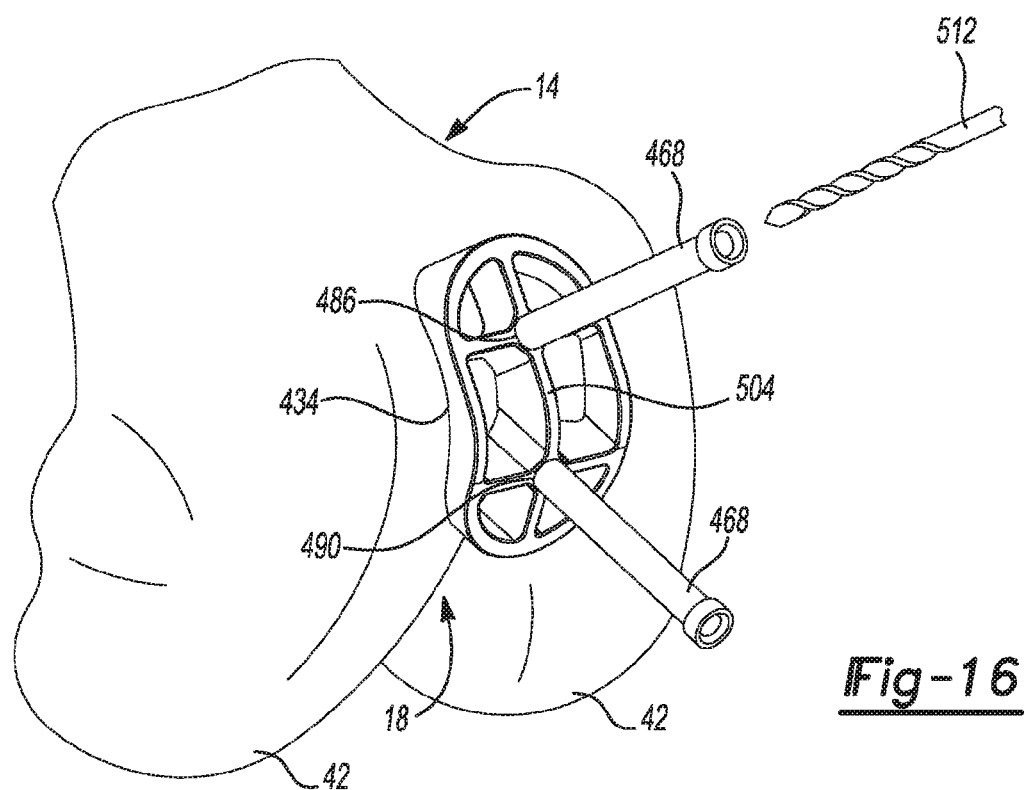
FIG. 16 is a perspective view of the exemplary procedure depicting a drill bit guided by the sizing drill guide to form a first bore in the femur in accordance with the teachings of the present disclosure.
Figure 17:
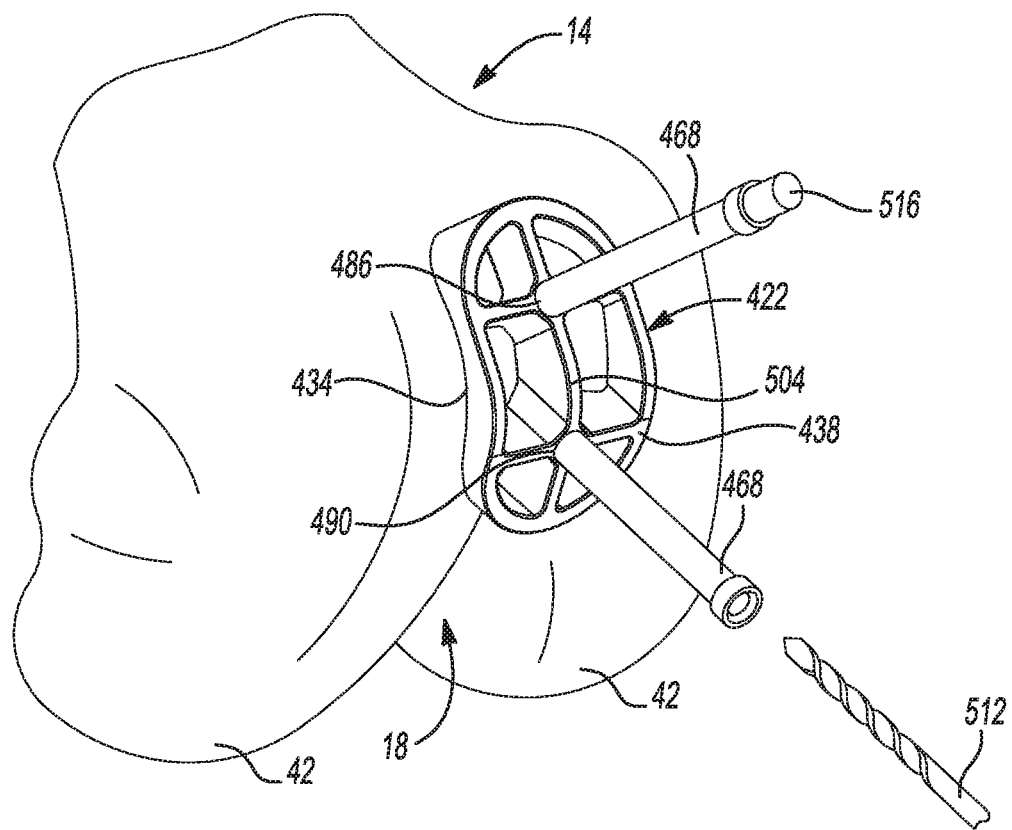
FIG. 17 is a perspective view of the exemplary procedure depicting a guide pin positioned in the first bore relative to the sizing drill guide and the drill bit guided by the sizing drill guide to form a second bore in the femur in accordance with the teachings of the present disclosure.

Once an appropriate sizing drill guide 422 has been selected that has a size corresponding to the size of defect 10 or that best matches with the size of the defect 10 and a bone engaging side overall profile 72 that corresponds to the anatomical configuration of the trochlear groove 18, the bone engaging side 434 can be positioned over defect 10 such that the profiles 64 nest in trochlear groove 18, as shown for example in FIGS. 1 and 16. With the sizing drill guide 422 positioned as discussed above, a cutting device, such as a drill bit 512 (FIG. 16) can be inserted into each of the cannulated guide members 468 and respective guide holes 486, 490 and into the femur 14. While not particularly shown in the drawings, drill bit 512 can include a shoulder or collar to set a drill depth relative to the sizing guide 422.

In the exemplary configuration illustrated, drill bit 512 can be advanced relative to the superior guide hole 486 and associated guide member 468 and into the femur to form a superior guide bore 524 (FIG. 19). The drill bit 512 can be removed and a guide pin 516 can be positioned through the cannulated guide member 468 and guide hole 486 and into bore 524 formed in femur 14. Guide pin 516 can temporarily fix the location of the sizing drill guide 422 on the femur 14 relative to the superior bore 524. With guide pin 516 in place, drill bit 512 can be positioned in guide hole 490 and its associated guide member 468 to drill an inferior guide bore 528 (FIG. 19) in femur 14. Guide pin 516 and sizing drill guide 422 can then be removed from femur 14.

Figure 18:
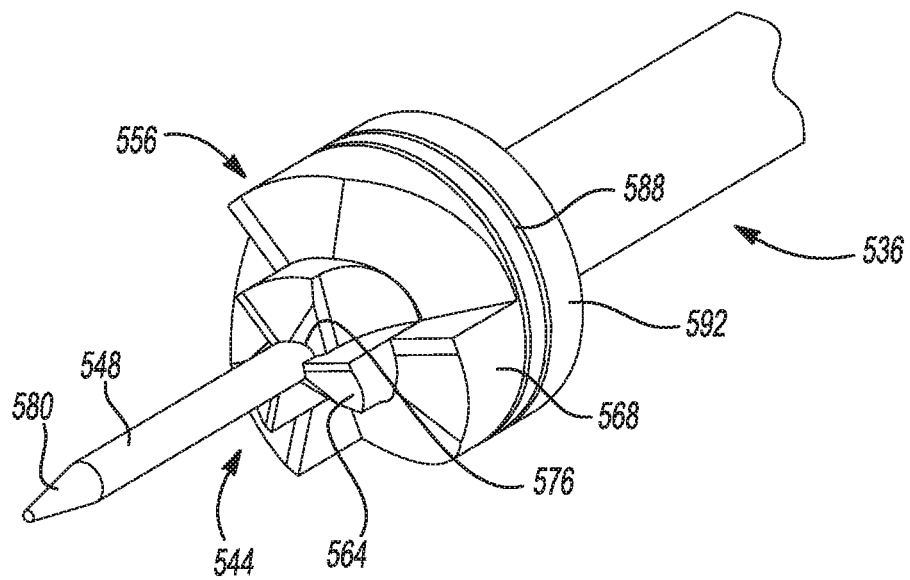
FIG. 18 is a perspective view of an exemplary drill bit or reamer in accordance with the teachings of the present disclosure.

With additional reference to FIGS. 18-20, a reamer 536 can be guided by formed guide bores 524, 528 to form portions of the femoral or trochlear pocket 126 (FIGS. 9 and 20). The reamer 536 can include a first or distal bone engaging end 544 and an opposite second or proximal end (not shown) configured to be coupled to a driver, such as a drill or other rotary driving instrument. The first end 544 can include a guide member 548 and a cutting or reaming arrangement 556 that can be similar to the cutting or reaming arrangement 138 of reamer 122. The reaming arrangement 556 can include a first cutting blade arrangement 564 and a second cutting blade arrangement 568. As can be seen in FIG. 18, the first cutting blade arrangement 564 can be concentric to and of a smaller diameter than the second blade cutting arrangement 568. In addition, in the exemplary configuration illustrated, the first cutting blade arrangement 564 can be axially spaced apart from the second cutting blade arrangement 568 so as to form the stepped pocket configuration of trochlear pocket 126 discussed above.

The bone engaging end 544 of reamer 536 can include the guide member 548 configured to guide reamer 536 relative to formed bores 524, 528. In one exemplary configuration, guide member 548 can project axially from a distal end 576 of first cutting blade arrangement 564 and can include a conical tip 580, as shown for example in FIG. 18. In the exemplary configuration illustrated, guide member 548 can include a diameter complimentary to the diameter of drill bit 512 and formed bores 524, 528, such that the formed bores can serve as a guide for reamer 536 when guide member 548 is positioned therein.

In use, reamer 536 can be separately positioned in each of formed bores 524, 528 to form the stepped pocket configuration show in FIG. 20, which can be the same stepped pocket configuration shown in FIG. 9 except for the formed bores 524, 528. In one exemplary aspect of the present teachings, the bone engaging end 544 of reamer 122 can be separately inserted into formed bores 524, 528 and advanced relative to femur 14 until depth indicia 588 on an outer body 592 is flush with the surrounding tissue. With continuing reference to FIGS. 9 and 20, this action can form the superior and inferior pocket portions 198, 182 of the stepped trochlear pocket 126 with the resultant geometry discussed above. Once the trochlear pocket 126 has been formed as discussed above in connection with sizing drill guide 422, corners 274 of the trochlear pocket 126 can be removed in a similar manner as discussed above in connection with the procedure related to sizing drill guide 22.

With continuing reference to FIG. 20 and reference back to FIGS. 6A-6C, once the trochlear pocket 126 is formed with sides 278, a trial corresponding to the selected sizing drill guide 422 can be positioned in the trochlear pocket 126 to check for proper fit in the manner discussed above. Once proper fit of the selected trial is established, the trial can be removed and trochlear pocket 126 can be cleaned and prepared for implantation of the corresponding implant 28 in a similar manner as also discussed above.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A system for use in repairing a soft tissue or bone defect, comprising:
    a combined sizing and drill guide adapted to be positioned relative to a trochlear groove of a femur, the guide including a body having a bone engaging side, an opposite side and defining first and second guide holes, wherein the bone engaging side includes a profile adapted to be positioned in the trochlear groove and the first and second guide holes include respective first and second axes that are orientated at an acute angle relative to each other;
    at least one retaining member configured to be positioned in a retaining bore formed in the body, the retaining member adapted to selectively fix the guide to the femur; and
    a cutting device configured to be selectively guided by the first and second guide holes, the cutting device including a bone engaging end having a body, a first cutting portion and a second cutting portion, the first cutting portion having a smaller diameter than the second cutting portion and being axially spaced apart therefrom so as to be adapted to form a stepped pocket in the femur, the body including an outer diameter portion sized to be complementary to an inner diameter of the first and second guide holes.

2. The system of claim 1, wherein the guide holes are spaced apart from each other on the opposite side and overlap each other on the bone engaging side.

3. The system of claim 2, wherein the guide holes include a superior guide hole and an inferior guide hole, and wherein an inferior portion of the superior guide hole and a superior portion of the inferior guide hole overlap each other on the bone engaging side such that each of the guide holes are truncated.

4. The system of claim 2, further comprising a femoral implant, the implant including a bone engaging side and an opposed articular surface side, the bone engaging side including a first perimeter forming an outer perimeter of the implant and a projection having a second perimeter smaller than the first perimeter, each of the first and second perimeters sized and shaped to be adapted to fit in the stepped pocket formed in the trochlear groove of the femur.

5. The system of claim 4, wherein the articular surface of the femoral implant is sized and shaped to mate with a size and shape of the profile of the bone engaging side of the combined sizing and drill guide.

6. The system of claim 4, wherein the opposite side of the guide includes a superior surface substantially perpendicular to the first axis and an inferior surface substantially perpendicular to the second axis.

7. The system of claim 6, wherein the reamer includes a depth control device selectively positionable along a shaft of the reamer, the depth control device having an engagement surface configured to selectively engage one of the superior and inferior surfaces to set a depth that the reamer can be advanced relative to the guide and the femur.

8. The system of claim 7, wherein the combined sizing and drill guide includes a plurality of combined sizing and drill guides each having a different bone engaging side profile and, wherein the femoral implant includes a corresponding plurality of femoral implants each having a different articular surface profile corresponding to the respective bone engaging side profiles of the plurality of guides.

9. The system of claim 8, wherein the articular surface profile of each implant of the plurality of implants is a negative of the bone engaging profile of the corresponding guide of the plurality of guides.

10. The system of claim 1, wherein the first guide hole is a superior guide hole and the second guide hole is an inferior guide hole positioned below the inferior guide hole when the guide is positioned relative to the trochlear groove.

11. The system of claim 10, wherein the at least one retaining member includes four retaining members, two of the retaining members positioned on lateral sides of the superior guide hole and two of the retaining members positioned on lateral sides of the inferior guide hole.

12. The system of claim 1, wherein the retaining bore is the first guide hole.

13. The system of claim 1, wherein the outer diameter portion is a guide member.

\* \* \* \* \*